United States Patent [19]

Chihiro et al.

[11] Patent Number: 5,295,833
[45] Date of Patent: Mar. 22, 1994

[54] DENTAL ROOT CANAL DIAGNOSTIC AND TREATING EQUIPMENT

[75] Inventors: Kobayashi Chihiro, Chiba; Kazunari Matoba, Kyoto, both of Japan

[73] Assignee: Kabushiki Kaisha Morita Seisakusho, Tokyo, Japan

[21] Appl. No.: 953,551

[22] Filed: Sep. 29, 1992

[30] Foreign Application Priority Data

Sep. 30, 1991 [JP] Japan .................. 3-280516

[51] Int. Cl.[5] .................. A61C 5/02; A61B 5/10
[52] U.S. Cl. .................. 433/224; 128/776
[58] Field of Search .................. 433/27, 119, 224; 128/776

[56] References Cited

U.S. PATENT DOCUMENTS

| | | | |
|---|---|---|---|
| 3,901,216 | 8/1975 | Felger | 433/27 |
| 3,916,529 | 11/1975 | Mousseau | 433/224 |
| 3,993,044 | 11/1976 | McGuffin | 433/224 |
| 4,177,799 | 12/1979 | Masreliez | 433/27 |
| 4,193,408 | 3/1980 | Kujino | 433/27 |
| 4,243,388 | 1/1981 | Arai | 433/27 |
| 4,353,693 | 10/1982 | Dery et al. | 433/224 |
| 4,428,748 | 1/1984 | Peyman et al. | 433/119 |
| 4,447,206 | 5/1984 | Ushiyama | 128/776 |
| 4,505,676 | 3/1985 | Gonser | 433/119 |
| 4,526,179 | 7/1985 | Salesky | 128/776 |
| 5,017,134 | 5/1991 | Saito et al. | 433/224 |
| 5,049,069 | 9/1991 | Salesky | 128/776 |
| 5,080,586 | 1/1992 | Kawai | 128/776 |
| 5,096,419 | 3/1992 | Kobayashi et al. | 128/776 |
| 5,112,224 | 5/1992 | Shirota | 433/224 |

*Primary Examiner*—Paul J. Hirsch
*Attorney, Agent, or Firm*—Koda and Androlia

[57] ABSTRACT

A dental root canal diagnostic and treating equipment with which specific position/s, which serve/s as the reference positions, can be set arbitrarily and such positions can be displayed. With the equipment, therefore, operation can be proceeded with knowledge of not only the position of the tip of the root canal instrument, which also serves as the measuring electrode, but also the remaining distance to the reference position.

7 Claims, 4 Drawing Sheets

DENTAL ROOT CANAL DIAGNOSTIC AND TREATING EQUIPMENT

BACKGROUND OF THE INVENTION

1. Field of the Invention

The present invention relates to improvement of a dental root canal diagnostic and treating equipment having a root canal length measuring function.

2. Description of the Prior Art

For treatment of root canal in dental practice a root canal instrument such as reamer or file is used for enlarging the root canal. The depth of the root canal enlargement, which is called "working length", is generally preferred to be up to −0.5 mm (up to 0.5 mm short of an apical position). It is, however, a usual practice that the operator sets it at a position considered optimum on the basis of his experience and in accordance with the therapeutic policy determined for the case or the technique selected therefor and in some extreme cases it is possibly set at −1 mm. When the operator does root canal enlargement by the use of a root canal diagnostic and treating equipment having a root canal length measuring function, it is necessary to do it confirming the position of the tool's tip by means of the display element of the equipment and stop the operation when his preset position has been reached.

With this kind of prior art equipment, however, generally used as display element is an analog meter of the pointer type or a like photoelectric meter. This type of meter is so designed that the displayed value increases steadily as a measuring electrode is inserted into the root canal and it agrees with the reading showing the apical position when the electrode has reached the apical position and has no function of displaying the working length set short of the apical position or of arbitrarily setting this working length.

Also, when a scaler of the ultrasonic type is used, it is necessary to stop or reduce the output of ultrasonic wave a little short of the aforementioned working length, but no conventional equipment has a function of setting and displaying the position at which the output is to be stopped or reduced ("changed" hereinafter). This output changing position is to be set as necessary according to the operator or his treating policy, the change is to be made according to the case, root canal condition, thickness of file used and whether the work to be done is enlargement or washing, and this change is done relatively frequently. Especially, since this root canal enlargement and washing by ultrasonic wave is known to be highly efficient, there is an increased risk of irregular enlargement taking place in the vicinity of the apical position when the output changing position cannot be grasped definitely or of steps or ledges being formed with the output changing position as boundary.

With a prior art equipment without function of displaying the working length or output changing position, therefore, it was necessary to proceed with the operation carefully grasping the position of the tip of the root canal instrument such as reamer or file by means of the display element and to change the output of ultrasonic wave or stop the operation at the present output changing position or working length without fail. This resulted in increased difficulty of operating the equipment and increased burden on the operator as well as lowering of the efficiency of diagnosis and treatment.

SUMMARY OF THE INVENTION

The present invention is aimed at solving such problems about the prior art. That is, the invention is aimed at improving the operability of the equipment by enabling arbitrary setting of the specific position which serves as criteria for root canal treatment as well as display thereof for improving the operability of the equipment. It is also aimed at provision of a root canal diagnostic and treating equipment easy to use with its display being readily readable. A further object of the invention is to automatically change the ultrasonic wave output when the root canal instrument has reached the pre-selected position to thus further make the equipment easier to use.

In order to accomplish the aforementioned objects, the dental root canal diagnostic and treating equipment having function to measure a root canal length comprises: a setting element which is capable of setting arbitrarily specific positions which serve as reference positions in the treatment of root canal, and a display means for displaying the set reference positions.

As the aforementioned reference position to be selected is at least any one of the working length position, apical position and the output changing position of a root canal treating equipment. As the aforementioned setting element may be used stepless variable element including a variable resistor or a stepwise variable element including a changeover switch or the like. The aforementioned display means is so constituted that display is made for either or both of the visual sense and the auditory sense and also that the display mode may be made different depending on the timing, i.e. either before the measuring electrode or the tip of the root canal instrument, which also serves as measuring electrode, reaches the aforementioned reference position or after reaching it.

When the above constitution is adopted, the operator can set the reference position according to his own therapeutic policy and, moreover, can have it displayed, so that he can proceed with operation properly, confirming the electrode's position and the remaining length to the reference position.

Further, when the dental root canal diagnostic and treating equipment is of the ultrasonic type, it is so designed that the output of the ultrasonic root canal diagnostic and treating equipment is automatically changed when the tip of the root canal instrument, which also serves as measuring electrode, has reached the predetermined one of the aforementioned reference positions. Then, it is no longer necessary to carefully monitor the position of the tip of the root canal instrument to change output manually near the apical position so as to make the equipment easy to operate.

DETAILED DESCRIPTION OF THE PREFERRED EMBODIMENTS

Hereinafter an illustrated embodiment of the invention will be described in detail.

Figure 1:
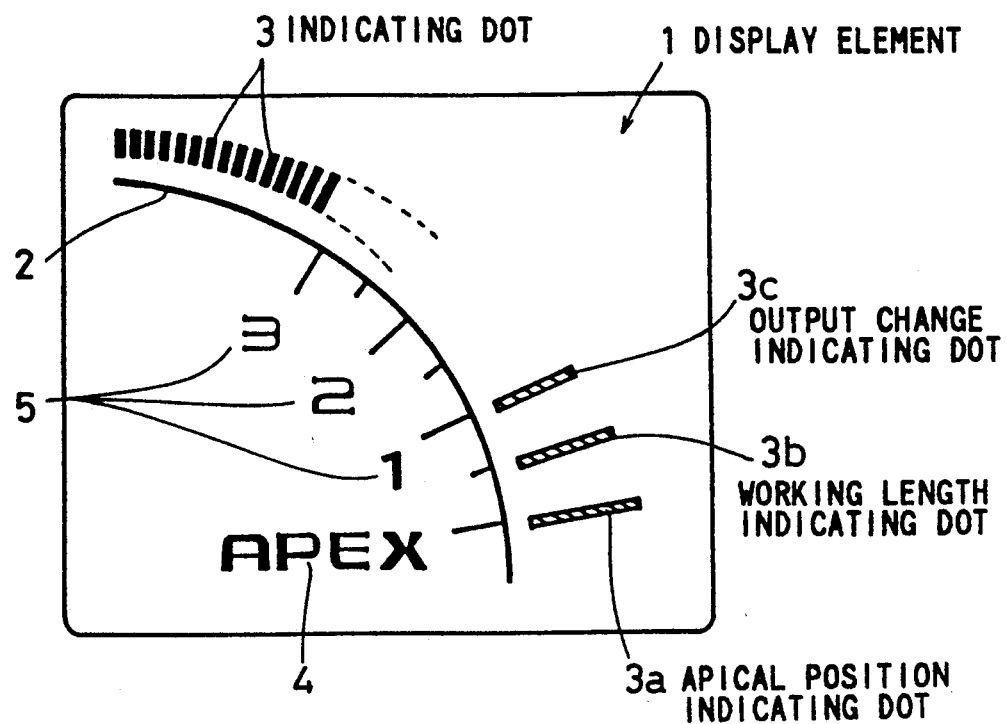
FIG. 1 is the front elevation of a display element in one embodiment of the present invention.
Figure 2:
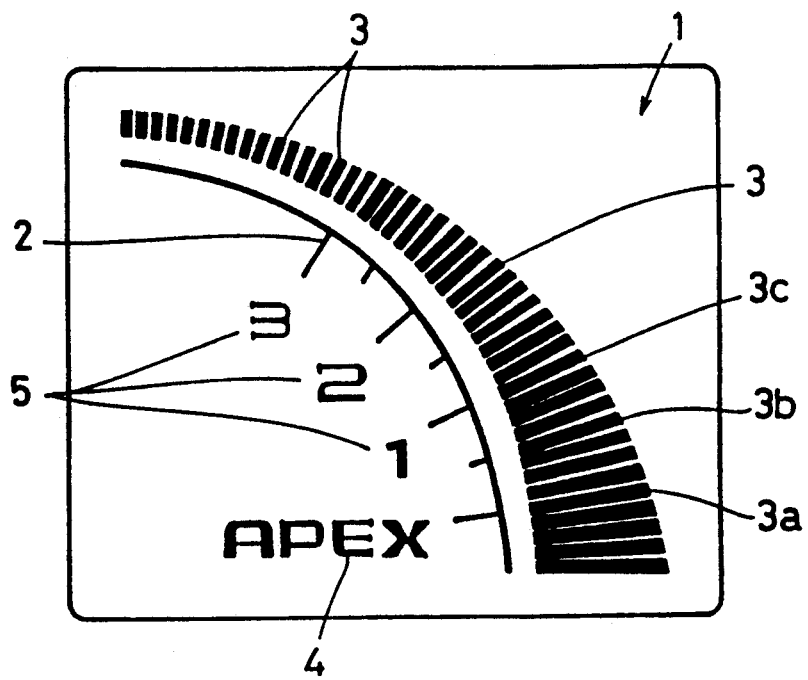
FIG. 2 is likewise the front elevation of the display element in one embodiment thereof.

In FIG. 1 and FIG. 2 reference numeral 1 represents one of display elements properly arranged in operation panels (not shown) of a diagnostic and treating equipment of the invention. Reference numeral 2 represents a scale, 3 a multiplicity of indicating dots along the scale 2, 4 an APEX mark disposed at one end of the scale 2 and 5 distance marks (unit: mm) disposed along the scale 2. 3a, 3b and 3c are what are selected from the indicating dots 3 for display of the specific reference positions, called apical position indicating dot, working length indicating dot and output change indicating dot respectively. Although the scale 2, indicating dots 3 and individual marks 4, 5 et cetera are formed of multi-color LEDs, these may as well be formed of LCDs or color monitors.

Figure 3:
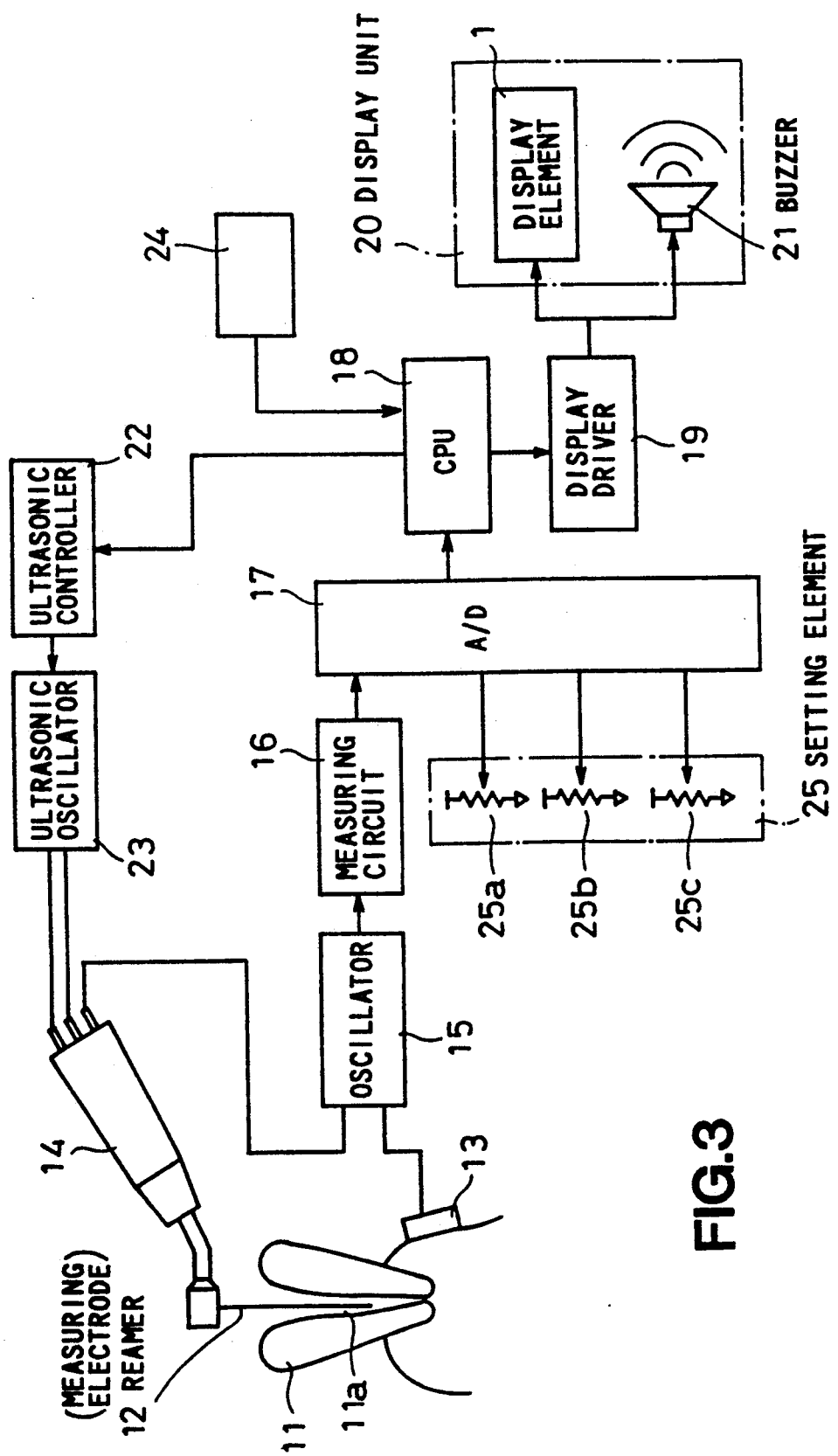
FIG. 3 is a block diagram showing an ultrasonic scaler provided with function to measure the root canal length in the same embodiment.

FIG. 3 is a block diagram of an ultrasonic scaler having a root canal length measuring function provided with such display element 1. As an equipment for electrically measuring the root canal length there is known that of a type detecting the resistance between a measuring electrode inserted into the root canal and an oral electrode connected with the oral soft tissue or of a type detecting the impedance between both electrodes. Although the present invention is applicable regardless of such types, the preferred embodiment is of the impedance detection type also provided with an ultrasonic circuit. The invention is also applicable to root canal diagnostic and treating equipment of the pneumatic vibration type or one using a micromotor.

In FIG. 3 reference numeral 11 represents a tooth, 11a its root canal, and 12 a root canal instrument such as a reamer of file also serving as the measuring electrode, the reamer in the illustrated case. 13 represents the oral electrode, 14 a hand piece holding the reamer 12, 15 an oscillator outputting measuring signals for detection of the impedance, 16 a root canal length measuring circuit for determining the root canal length from the detected impedance response value, 17 an A-D converter, 18 a CPU, 19 a display output driver and 20 a display unit provided with, beside the above-mentioned display element 1, a buzzer 21 emitting signal sounds. 22 is an ultrasonic output controller, 23 an ultrasonic oscillation circuit and 24 an indicating element.

CPU 18 is so programmed that ultrasonic output is controlled by the signals it sends to an ultrasonic wave output controller 22 and the display unit 20 is controlled thereby to do display action as described below and the instructions about ultrasonic output adjustment, whether the ultrasonic output is to be changed or about the mode of operation of the equipment as a whole et cetera are inputted by an indicating element 24 to CPU 18.

Reference numeral 25 represents the setting element provided with a variable resistor 25a for indicating the apical position, another variable resistor 25b for setting the working length and still another variable resistor 25c for setting the output changing position. These variable resistors are properly arranged on the operation panel so as to be easily operable by the operator and the set position is inputted to CPU 18 via A-D converter 17. Thus, the indicating dots 3 corresponding to the set positions are used as the apical position indicating dots 3a, the working length indicating dots 3b and the output change indicating dots 3c respectively.

Figure 4:
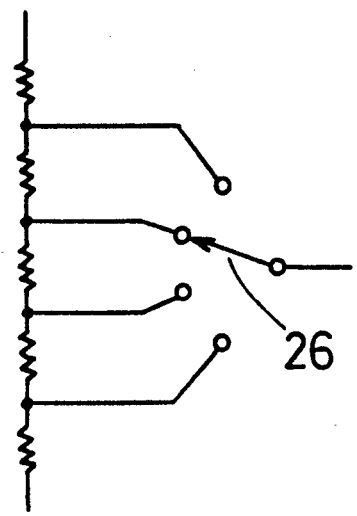
FIG. 4 is a circuit diagram in another setting element in the same embodiment.

Although in FIG. 3 a variable resistor is used in the setting element 25, it is also possible to use a stepwise variable element 26 e.g. changeover switch as illustrated in FIG. 4 instead of a stepless movable element using such variable resistor.

The indicating dots 3 are so designed that as the measuring electrode 12 is inserted into the root canal 11a, the dots are lit successively beginning from the left upper-most one, and the apical position indicating dot 3a, the working length indicating dot 3b and the output change indicating dot 3c are lit in a mode different from other dots. For example, the color of the indicating dots 3 is blue when lit and those selected as the working length indicating dot 3b and the output change indicating dot 3c are made to flicker, while the apical position indicating dot 3a, which also flickers, is red when lit for alarming.

FIG. 1 shows the condition when the reamer 12 has been inserted halfway and FIG. 2 shows the condition when the reamer 12 has been inserted a little beyond the apical position respectively. With a prior art counterpart it was so designed that the number of the indicating dots 3 increased linearly as the reamer 12 was inserted and the operator finished measurement of the root canal length when the indicating dots 3 have been lit up to the APEX mark or, for example, to two dots short of the APEX mark and the position so determined was taken as the apical position or as the working length. In contrast thereto, in the embodiment of the invention the apical position, the working length and the output changing position can be set arbitrarily and these are displayed by flickering of the apical position indicating dot 3a, the working length indicating dot 3b and the output change indicating dot 3c respectively.

In the illustrated example the working length is set −0.5 mm off the apical position and the output changing position −1 mm off the apical position, and in FIG. 1 shown is the condition under which there remains a distance of approx. 2.5 mm until the working length is matched.

When the reamer 12 is inserted under this condition, the indicating dots 3 are lit successively and, when it has been checked that the tip of the reamer 12 has reached the output changing position, an output change signal is sent from CPU 18 to the ultrasonic output controller 22 for the ultrasonic oscillation to be stopped or for the oscillation output to be lowered. Then the output change indicating dot 3c ceases flickering to be lit continuously with simultaneous sounding of a buzzer 21 emitting, for example, short sound signals in slow cycles for announcing change of the output.

When it has been detected that the tip of the reamer 12 has reached the working length position, the working length indicating dot 3b ceases flickering to be lit continuously with simultaneous shortening of the cycles of the sound signals for announcing arrival of the working length position. When the reamer 12 has been further inserted to reach the apical position, the apical position indicating dot 3a ceases flickering to be lit continuously with simultaneous change of the sound signal of the buzzer 21 to become a continuous one for announcing arrival of the reamer 12 at the apical position.

The above mode of display is a mere example and the mode of lighting of the individual dots 3 and the way the buzzer 21 emits the sound signal may as well be different from the examples above. It may as well be possible to use a voice message by the use of a voice synthesizer instead of the buzzer 21. It is also possible to operate the buzzer 21 before it reaches the output changing position or to use either of the display means for visual sense such as the indicating meter and the display means for auditory sense such as the buzzer 21.

Although in the embodiment changing of the ultrasonic output is done at a point different from the apical position and the working length, it may, as necessary, be made at the same position as the apical position or the working length position and it is also possible to change the output at this position.

Figure 5:
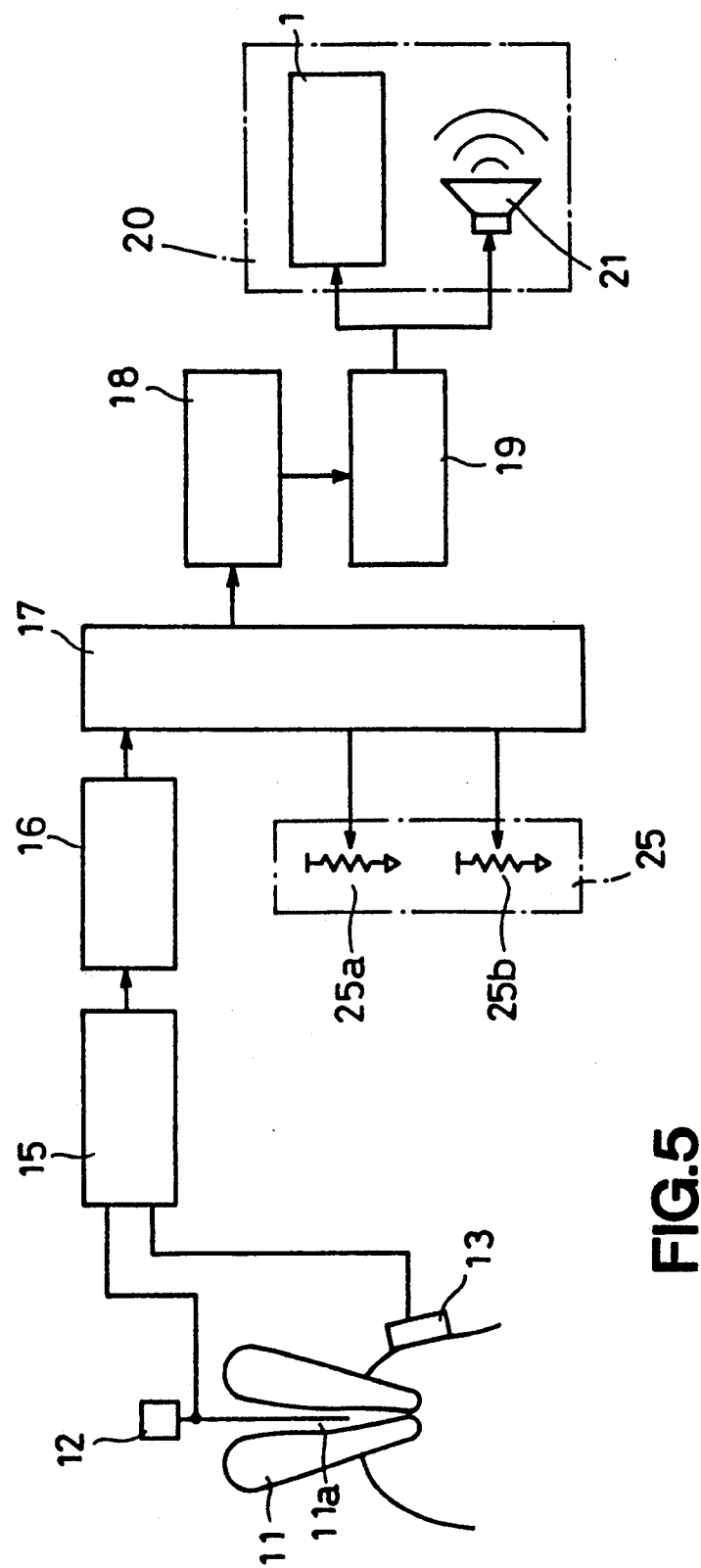
FIG. 5 is a block diagram of a root canal length measuring device in another embodiment of the invention.

Although 3 reference positions are set in the embodiment described above, it does not mean that the number of the reference positions is limited to three and a proper number thereof may be set arbitrarily. FIG. 5 shows an example in which ultrasonic functions are eliminated from those of the embodiment of FIG. 3 and the apical position and the working length are set as the reference positions. In this case the apical position indicating dot 3a and the working length indicating dot 3b are displayed on the display element 1 as the reference positions.

Although a photoelectric meter is used in the above-mentioned embodiment, an analog meter of the pointer type may as well be used if a pointer for indicating the reference position is added and its position is made to be set arbitrarily.

Figure 6:
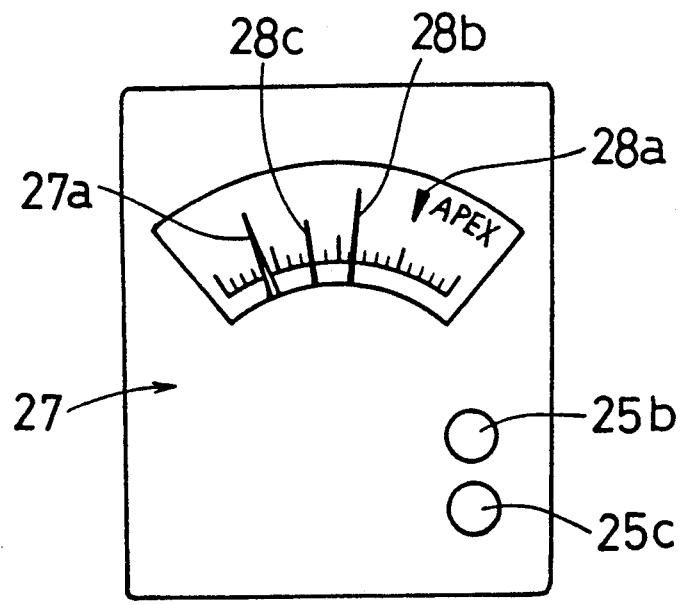
FIG. 6 is a front elevation showing another display element.

FIG. 6 shows an example of analog meter provided with a plurality of pointers distinguishable from one another by color, shape, length et cetera, in which reference numeral 27 represents a pointer-type meter, 27a a movable pointer, 28a an apical position mark, 28b a working length indicating pointer and 28c an output change indicating pointer. In this example the apical position indicating pointer is fixed, the working length position and the output changing position are indicated by the individual pointers 28b and 28c and the movement of the measuring electrode is indicated successively by the movable pointer 27a. The positions of the pointers 28b and 28c are made to set interlockingly with the variable resistors 25b and 25c. It is also possible to make it of the meter-relay type, in which the indicating pointers 28b and 28c are made directly movable by means of, for example, mechanical control element and the reference positions can be set electrically according to the positions of the pointers.

What is claimed is:

1. A dental root canal diagnostic and treating equipment having a function to measure a root canal length, comprising:
    a setting means for setting arbitrarily specific positions which serve as preset reference positions in the treatment of root canal, and
    a display means for displaying the preset reference positions during diagnosis and treatment of a root canal.

2. A dental root canal diagnostic and treating equipment according to claim 1, wherein said preset reference positions are at least one of the group consisting of working length position, apical position and output changing position.

3. A dental root canal diagnostic and treating equipment according to claim 1 or 2, wherein said setting means is a stepless variable element using a variable resistor.

4. A dental root canal diagnostic and treating equipment according to claim 1 or 2, wherein said display means is made for displaying either or both of visual mode and auditory mode and said display means is constituted such that the display mode is different before or after the tip of a measuring electrode or a root canal instrument which also serves as a measuring electrode reaches said preset reference positions.

5. A dental root canal diagnostic and treating equipment according to claim 1 or 2, wherein said diagnostic and treating equipment is a root canal treating equipment of the ultrasonic type and it is so arranged that the output of the ultrasonic root canal treating equipment is automatically stopped or reduced upon arrival of the tip of the root canal instrument, which also serves as the measuring electrode, at a pre-selected one of said preset reference positions.

6. A dental root canal diagnostic and treating equipment according to claim 1 or 2, wherein said setting means comprises a stepwise variable element using a changeover switch.

7. A dental root canal diagnostic and treating equipment according to claim 1 wherein said display means further displays a position of a tip of a measuring electrode or a root canal instrument which serves as the measuring electrode.

* * * * *

UNITED STATES PATENT AND TRADEMARK OFFICE
CERTIFICATE OF CORRECTION

PATENT NO. : 5,295,833
DATED : March 22, 1994
INVENTOR(S) : Chihiro Kobayashi, et al.

It is certified that error appears in the above-identified patent and that said Letters Patent is hereby corrected as shown below:

On the Title Page:

Item [75] Inventors: Change "Kobayashi Chihiro, Chiba; Kazunari Matoba, Kyoto, both of Japan" to --Chihiro Kobayashi, Chiba; Kazunari Matoba, Kyoto, both of Japan--

Item [73] Assignee: Change "Kabushiki Kaisha Morita Seisakusho, Tokyo, Japan" to --Kabushiki Kaisha Morita Seisakusho, Kyoto, Japan--

Item [30] Foreign Application Priority Data:

Add --August 27, 1992 [JP]  Japan .............. 4-254160--

Signed and Sealed this

Twelfth Day of July, 1994

Attest:

BRUCE LEHMAN

*Attesting Officer*    *Commissioner of Patents and Trademarks*